US006723690B1

(12) United States Patent
Aronson et al.

(10) Patent No.: US 6,723,690 B1
(45) Date of Patent: *Apr. 20, 2004

(54) PROCESS FOR MAKING EXTRUDED MULTIPHASE BARS EXHIBITING ARTISAN-CRAFTED APPEARANCE

(75) Inventors: Michael Paul Aronson, West Nyack, NY (US); Badreddine Ahtchi-Ali, Martinsville, NJ (US); Sergio Roberto Leopoldino, Sousas (BR); Gregory Jay Mc Fann, North Bergen, NJ (US); Mariangela Gomes De Oliveira Sichmann, Campinas (BR)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/340,153

(22) Filed: Jan. 10, 2003

(51) Int. Cl.[7] .................................................. A61K 7/50

(52) U.S. Cl. ....................... 510/146; 510/141; 510/147; 510/148; 510/152; 510/153; 510/155; 510/449

(58) Field of Search ................................ 510/147, 148, 510/152, 449, 141, 146, 151, 153, 155

(56) References Cited

U.S. PATENT DOCUMENTS

| | | | | |
|---|---|---|---|---|
| 3,673,294 A | | 6/1972 | Matthaei | |
| 3,884,605 A | | 5/1975 | Grelon | |
| 3,940,220 A | | 2/1976 | D'Arcangeli | |
| 3,993,722 A | | 11/1976 | Borcher et al. | |
| 4,092,388 A | | 5/1978 | Lewis | |
| 4,310,479 A | | 1/1982 | Ooms et al. | |
| 5,935,917 A | | 8/1999 | Farrell et al. | |
| 5,965,501 A | * | 10/1999 | Rattinger et al. | 510/146 |
| 5,972,859 A | | 10/1999 | Farrell et al. | |
| 5,981,464 A | | 11/1999 | He et al. | |
| 6,383,999 B1 | | 5/2002 | Coyle et al. | |
| 6,390,797 B1 | | 5/2002 | Myers | |

OTHER PUBLICATIONS

Aronson et al., 10/340,468, Jan. 10, 2003, Methods of Cleaning Moisturizing and Refreshing Using Multiphase Bars Having Artisan–Crafted Appearance.

Aronson et al., 10/340,457, Jan. 10, 2003, Extruded Multiphase Bars Exhibiting Artisan–Crafted Appearance.

* cited by examiner

*Primary Examiner*—Necholus Ogden
(74) *Attorney, Agent, or Firm*—Ronald A. Koatz

(57) ABSTRACT

The present invention relates to a process for making a multiphase personal wash bar having artisan crafted appearance. The bars are made by combining the second solid mass phase to a first continuous phase wherein the hardness of the second phase is at least twice the hardness of noodles forming the continuous phase.

6 Claims, No Drawings

PROCESS FOR MAKING EXTRUDED MULTIPHASE BARS EXHIBITING ARTISAN-CRAFTED APPEARANCE

FIELD OF THE INVENTION

The invention relates to multiphase personal washing bars having an artisan-crafted appearance, and, more particularly, to high throughput extrusion processes for making such bars which are suitable for everyday use. The bars made by the process comprise a discontinuous phase having its longest dimension between about 3 and about 75 mm that is dispersed in a continuous phase containing a cleansing base. By ensuring the hardness of the continuous phase is within certain limits, and that the ratio of the hardness of the two phases measured at specific temperatures is greater than a critical value, it is possible to extrude the composition at high speed (e.g., at least about 200 bars/minute, preferably in excess of 300 bars/minute) while maintaining spatially distinct regions at the surface of the bar as measured by a visual discrimination panel test. Plasticizing and hardening agents that can be used to alter the rheology of the phases in order to meet these constraints are described.

BACKGROUND

Multicolor or multiphase soaps have been described by various terms that include variegated, marbled, striated, and striped. Prior art has mainly focused on routes to reproducibly achieve spatial variation in dye or pigment concentration as the primary means of generating bars that appear as comprising multiple phases.

Key technical problems that were recognized early in the commercial exploitation of such bars were: efficient manufacture with consistent patterns; distinctive contrast between the different colors especially at the bar surface; and the elimination of cracking, fissuring, and color migration ("bleeding") during storage and use. Commercial processes and machines are now available to produce multicolor soaps that have highly consistent appearance.

The multicolor nature of the prior art bars gives the impression that the bars comprise distinct phases that have different ingredients or function. However, the vast majority of multicolored bars disclosed in the art and sold in the mass market have virtually homogeneous composition and few different properties apart from gradients in coloring agents. Incomplete mixing during manufacture of the bar essentially produces these dye gradients.

With the resurgence in the specialty soap market, consumers are being offered multicolor/multiphase bars that have a much more hand crafted (i.e., "artisan crafted") "one-of a kind" appearance. Technically such bars have at least the following three characteristics that contribute to their distinctive appearance: i) The sharpness of the boundary between the phases; ii) an easily recognizable difference in optical texture and/or pattern that goes beyond color, and iii) a certain degree of bar to bar non-uniformity. Differences in optical texture and pattern are especially important to convey a collection of sensory expectations associated with that phase. Examples include translucency, shine, and sharp edges to convey a gel; circular dark patterns or repeating textures to convey fruit, etc.

Artisan soaps are predominantly made by cast melt processes—either single casting or sequential multiple casts. Because these cast melt processes are slow and labor intensive, multiphase artisan soaps are relatively expensive and confined to upscale specialty shops and outlets.

Furthermore, cast melt soaps are known to have high wear rates and mushing characteristics that make them less preferred for everyday use.

One objective of the present invention is a multiphase bar soap that has an artisan-crafted appearance yet can be produced by a conventional high speed (e.g., at least about 200 bars/minute) extrusion process with only minor equipment modifications and requires minimum (preferably no), trimming.

A second objective is an extruded multiphase soap wherein the phases have sharp boundaries, recognizable differences in optical texture and pattern, and different composition.

A third objective is a multiphase soap having an artisan-crafted appearance that has in-use properties and unit-cost that will make it suitable for the mass market.

A still further objective is the production of extruded multiphase soap bars that will have adequate bar to bar variability to convey distinctiveness.

Another specific objective of the subject invention is a process for making such bars.

As will be shown, these and other objectives can be met by following the teachings of the present invention.

BACKGROUND

U.S. Pat. No. 3,673,294 to Matthaei et al, teach a process to form multicolored bars by extruding a mixture of two noodles which are required to have the same viscosity and essentially the same hardness (penetration value).

U.S. Pat. No. 3,940,220 to D'Arcangeli teaches the extrusion of a mixture of two noodles in which it is required that the discontinuous phase be softer (lower penetration value) than the main soap. In the bars made by the process of subject invention, the discontinuous phase is harder.

U.S. Pat. No. 3,993,722, to Borcher et al and U.S. Pat. No. 4,092,388 to Lewis teach processes of combining different colored noodles to formed marbled soap. The two noodles have essentially the same composition (e.g., hardness) apart from colorant and the two different color noodles have essentially the same temperature at the time of extrusion.

U.S. Pat. No. 4,310,479 to Ooms et al teaches a process for combining a minor amount of opaque noodles with transparent noodles to form a transparent marbled bar. The noodles should differ in water content by no more than 3% and are at the same temperature during extrusion. Accordingly, hardness of the noodles and bar is about the same.

U.S. Pat. No. 6,390,797 to Meyers teaches a process for making marbleized or speckled soap by addition of a second stream of colored soap pellets into the interior of the final stage plodder at a specific point. No mention is made about the hardness of the two phases or their required properties or of processes of making bars of the invention.

U.S. Pat. No. 3,884,605 to Grelon teaches an apparatus for making striated soap made by coextrusion where it is desirable that the two soaps have identical material properties, e.g., hardness, apart from color.

U.S. Pat. No. 6,383,999 to Coyle et al teach a coextruded multiphase bar in which the phases differ in the level of emollient but must have similar flow properties under extrusion process conditions.

U.S. Pat. No. 5,935,917 to Farrell et al, U.S. Pat. No. 5,972,859 to Farrell et al and U.S. Pat. No. 5,981,464 to He et al teach bar compositions comprised of surfactant chips mixed with a second chip comprised predominantly of polyether and containing an emulsified benefit agent. The polyether chips are friable by design so that they disperse when mixed with the soap chips.

None of these patents teach that the discontinuous phase of a multiphase bar should be at least twice as hard as the soap mass that will become the continuous phase of the bar when these two phases first come into contact prior to the final extrusion. For example many patents teach the combining of different color noodles in the vacuum chamber of a two state refiner-plodder. However none of these patents teach that one noodle should be at leas twice as hard as the other colored noodle when these noodles are initially combined.

Further the art does not teach appropriate plasticizers and hardening agents that enable these rheological requirements to be met. In fact the large majority of the prior art emphasize engineering approaches (apparatus and different processes) to overcome problems in making acceptable multicolor soaps using soaps of uniform composition apart from coloring agents.

BRIEF DESCRIPTION OF THE INVENTION

The subject invention describes multiphase personal washing bars that have a artisan-crafted appearance that can be made in a high speed extrusion process by ensuring that the hardness of the discontinuous phase is sufficiently greater than the continuous phase so that it does not excessively deform during extrusion.

More specifically, the invention comprises:

a) a continuous solid phase covering about 65% to 99% by wt final bar composition and comprising 25–90% of the continuous phase composition of a surfactant base suitable for cleansing the skin, b) a discontinuous phase (present as one or more "domains" of discontinuous phase within the continuous phase) comprising about 1 to about 35% of final bar composition and that comprises a water soluble or water dispersible solid matrix comprising at least 1 wt % surfactant wherein said discontinuous phase has its longest dimension between about 3 and about 75 mm, wherein the hardness of the continuous phase is in the range of 1.9 to 2.5 bar. (1 bar equals 100,000 Pascals) when measured at a temperature between 33 and 50° C., preferably 30 and 42° C. wherein the ratio, $\lambda$, defined as the hardness of the discontinuous phase measured at a temperature of 25° C. divided by the hardness of the continuous phase measured at a temperature of 33° C. is greater than 2.0; and wherein said hardness values are measured by the Cylinder Impaction Test;

wherein the discontinuous phase comprises 1 to about 25 wt % of the bar, and wherein the bar has a descriptive visual grading score of at least 3.0 when measured by Visual Discrimination Panel Test.

The temperature noted above approximately reflects the thermal conditions of each phase during the time of extrusion and, without wishing to be bound by theory, when these conditions are met, the discontinuous phase is believed to not deform excessively, under shear, and therefore, is believed to allow formation of the artisan-type bars.

A second embodiment of the invention, comprises a process for making a bars having an artisan crafted appearance by extrusion wherein said process comprises:

1) adding to noodles comprising the continuous phase of a toilet bar mass that is at a temperature about 33 to 50° C., a second solid mass that is in the form of discrete particles having at least one dimension greater that 3 mm to form a mixture, wherein at the time of addition, the hardness values measured by the Cylinder Impaction Test;

2) extruding the mixture so formed in step 1) to form an extruded composite mass comprising a continuous toilet bar mass and a disontinuous phase of the second solid mass;

3) cutting and forming the extruded mass into a bar wherein the discontinuous phase comprises 1 to about 25 wt % of the bar, and wherein the bar has a visual grading score of at least 3.0 when measured by Visual Discrimation Panel Test.

BRIEF DESCRIPTION OF THE DRAWINGS

DETAILED DESCRIPTION OF THE INVENTION

The bars of this invention comprise a continuous phase and a discontinuous phase. A critical aspect of the invention is that the hardness of these phases meet specific requirements. In a second embodiment, the invention comprises preparing a continuous phase and discontinuous phase solid mass (defined by difference in hardness), adding together in a mixer at defined temperature range, extruding, and cutting to form final bars. The bars and component phases are discussed in greater detail below

Continuous Solid Soap Phase

The continuous phase comprises 65 wt % to about 99 wt % of the bar composition, preferably 75 wt % to 95 wt % and most preferably 80 to 90 wt %. A key requirement is that the hardness as measured by the Cylinder Impaction Test described below has a value falling in the range of 1.9 to 2.5 bars when measured at a temperature between 33 and 42° C. It has been found from experience that when the hardness of the continuous phase falls within this range, it is possible to form bars by extrusion at a high rate. By high rate is meant in excess of 200 bars per minute and preferably greater than 300 bars per minute.

The continuous phase comprises a surfactant or detergent base suitable for cleaning the skin and optionally a plasticizing agent used to control its consistency.

It has also been found preferable for the continuous phase to have a certain degree of plasticity so that it adheres well to the discontinuous phase. The plastic zone size, r, as measured by Three-Point Bend Test described in the Test Methodology section provides a relevant measure of plasticity or brittleness. The continuous phase should have a plastic zone radius greater than 2.0 mm and preferably greater than 2.5 mm. A lower value of the plastic zone size represents a continuous phase sample that is more brittle, a greater value represents a more plastic sample.

It has been found that when the plastic zone radius of the continuous phase is greater than 2.0 mm, a cohesive bar junction between the continuous and discontinuous phase is favored, i.e., the bars don't crack

Surfactant Base

The primary component of the continuous phase is a surfactant base suitable for cleansing the skin. Generally the surfactant base comprises 25–90 wt % of the continuous phase, preferably between 50 and 80 wt %.

One useful surfactant base comprises fatty acid soaps. The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of acrylic hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 30% to about 40% coconut oil and about 60% to about 70% tallow. Mixtures may also contain higher amounts of tallow, for example, 15% to 20% coconut and 80 to 85% tallow.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

A second type of surfactant base useful in the practice of this invention comprises non-soap synthetic type detergents—so called syndet bases.

Anionic Surfactants

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation; and amido-MIPA sulfosuccinates of formula $$RCONH(CH_2)CH(CH_3)(SO_3M)CO_2M$$

where M is as defined above.

Also included are the alkoxylated sulfosuccinates; wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R—(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ(R) by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application.

Another surfactant which may be used are $C_8$ to $C_{22}$ neutralized fatty acids (soap). Preferably, the soap used are straight chain, saturated $C_{12}$ to $C_{18}$ neutralized fatty acids.

In general the anionic component will comprise from about 1 to 20% by weight of the composition, preferably 2 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

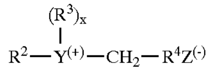

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

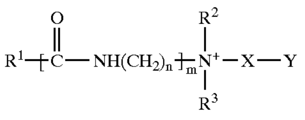

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric detergents within the above general formula include simple betaines of formula:

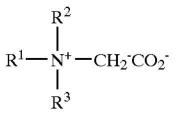

and amido betaines of formula:

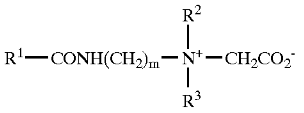

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

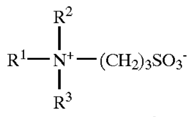

or

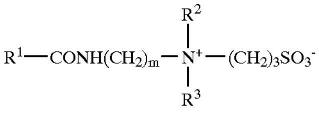

where m is 2 or 3, or variants of these in which $—(CH_2)_3SO^-_3$ is replaced by

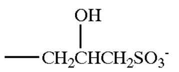

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Examples of cationic detergents are the quaternary ammonium compounds such as alkyldimethylammonium halogenides.

Other surfactants which may be used are described in U.S. Pat. No. 3,723,325 to Parran Jr. and “Surface Active Agents and Detergents” (Vol. I & II) by Schwartz, Perry & Berch, both of which is also incorporated into the subject application by reference.

Although the surfactant may be a pure soap base or a pure syndet base it is in some cases preferable to uses a combination of soaps with synthetic detergents. Examples of combination bases are disclosed in U.S. Pat. No. 4,695,395 to Caswell, et al.

Plasticizing Agents (e.g., in continuous phase)

It is may be possible to tailor the surfactant base so that its hardness is in the required range, e.g., by adjusting the titre of the fat charge (softening) in the case of soap or the water content. However, this can often compromise user properties and impact cost. Consequently a second very useful component of the continuous phase is a plasticizing agent. Here we define plasticizing agent as a material that may alter both the hardness and the consistency (e.g., the plastic radius) of the continuous phase, especially at temperatures at which the multiphase bar is extruded and stamped. Without being bound by theory, these materials are thought to facilitate the flow of the continuous semi-solid mass around the dispersed phase during final extrusion and compaction so that a strong bond between these phases is formed. These agents also help reduce the debonding of the two phases that can lead to cracking or pitting during use.

A variety of materials can be used as a plasticizer: the key property is that they alter the consistency of the continuous phase mass, when it is combined with the discontinuous phase.

Oils are particularly useful plasticizers. One useful class of oils is ester oils: oils having at least one ester group in the molecule, especially fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and the like.

Triglycerides and modified triglycerides are particularly useful ester oils. These include vegetable oils such as jojoba, soybean, canola, sunflower, palm, safflower, rice bran, avocado, almond, olive, sesame, persic, castor, coconut, and mink oils. These oils can also be hardened to remove unsaturation and alter their melting points. Synthetic triglycerides can also be. Some modified triglycerides include materials such as ethoxylated and maleated triglyceride derivatives provided. Proprietary ester blends such as those sold by Finetex as Finsolv® are also suitable, as is ethylhexanoic acid glycerides.

Another type of useful ester oil is liquid polyester formed from the reaction of a dicarboxylic acid and a diol. An example of polyesters suitable for the present invention is the polyesters marketed by ExxonMobil under the trade name PURESYN ESTER®.

A second class of oils suitable for the present invention is hydrocarbon oil. This includes linear and branched oils such as liquid paraffin, squalene, squalane, mineral oil, low viscosity synthetic hydrocarbons such as polyalphaolefin sold by ExxonMobil under the trade name of PureSyn PAO® and polybutene under the trade name PANALANE® or INDOPOL®. Highly branched hydrocarbon oils may also be suitable. Although more properly classified as a grease, petrolatum can also serve as a useful plasticizer.

Some natural and synthetic waxes can also be used as plasticers providing they have the correct melting point and solubility properties with the continuous phase.

A third type of material that can function as a plasticizer are C8–C22 fatty acids, preferably C12–C18, preferably saturated, straight-chain fatty acids. However, some unsaturated fatty acids can also be employed. Of course the free fatty acids can be mixtures of shorter (e.g., C10–C14) and longer (e.g., C16–C18) chain fatty acids although it is preferred that longer chain fatty acids predominate over the shorter chain fatty acids.

The fatty acid can be incorporated directly or be generated in-situ by the addition of protic acid. Examples of suitable protic acids include: HCL, adipic acid, citric acid, glycolic acid, acetic acid, formic acid, fumaric acid, lactic acid, malic acid, maleic acid, succinic acid, tartaric acid and polyacrylic acid. Other protic acids are mineral acids such as hydrochloric acids, phosphoric acid, sulfuric acid and the like.

Nonionic surfactants can also serve as plasticizers for the continuous phase. Nonionic surfactant in the context of instant invention are amphiphilic materials in which the polar groups are uncharged. Examples of suitable nonionic surfactants include: ethoxylates (6–25 moles ethylene oxide) of long chain (12–22 carbon atoms) fatty alcohol (ether ethoxylates) and fatty acids; alkyl polyhydroxy amides such as alkyl glucamides; alkyl polyglycosides; esters of fatty acids with polyhydroxy compounds such as glycerol and sorbitol; ethoxylated mon-, di- and triglycerides, especially those that have lower melting points; and fatty amides.

Organic bases, especially alkoxy amines like triethanolamine are also useful plasticizers when the surfactant base is soap.

In addition to modulating hardness, the palsticizing agent also helps reduces the consistency of the continuous mass at the extrusion and compaction steps in the process thereby improving the bonding to the discontinuous phase as well as flow around the discontinuous phase at the surface.

Discontinuous Phase

The discontinuous phase comprises from 1 to about 35% of the bar, preferably from 5 to 25%, and most preferably from 10 to 20%. It is generally the shape, distribution and surface quality (e.g., how visually distinctive) of the diconinuous phase that gives the bar an artisan-crafted quality.

The discontinuous phase forms discrete domains in the bar and comprises a water-soluble or water-dispersible matrix and optionally a hardening agent. By water-soluble or water-dispersible is meant the ability of the matrix to disintegrate and disperse when the bar is rubbed against the skin in the presence of water during use. A convenient measure of this property is the intrinsic wear rate the matrix material exhibits under controlled rubbing conditions as described in the Test Methodology section. A suitable matrix should have an intrinsic wear rate between 0.012 and 0.05 gm/cm2, preferably 0.02 to 0.03 gm/cm2, when measured by the Controlled Rubbing Test. Thus, for example material like polyethylene could be used a component of the matrix, e.g., as small beads, but is not suitable by itself as the matrix because its intrinsic wear rate is essentially zero.

The discontinuous phase domains can have a variety of shapes. For example, the domains can appear in cross section to approximate oblate or prolate spheroids, disks, cylinders, prisms, rhomboids, cubes or crescents. They can also have irregular shapes. However, a unifying feature is that their longest dimension be between about 3 and about 70 millimeters in length, preferably 5 to 50 and most preferably between 5 and 35 millimeters.

A key requirement is that the ratio, λ, defined as $$\lambda = \frac{\text{Hardness of Discontinous Phase@25° C.}}{\text{Hardness of Continous Phase@33° C.}}$$

is greater than 2.0, preferably greater than 2.5, and most preferably greater than 3.0. Here the hardness is measured by the Cylinder Impaction Test described in the Test Methodology section below. There are several methods known in the art to measure the hardness of material like soaps. The Cylinder Impaction Test is a convenient measure in a manufacturing context. However, other measures like the Penetrometer Test described in the Methodology Section can also be employed and the values correlated to the Cylinder Impaction Test. The key point is that the hardness ratio of the two phases measured at temperatures approximating the temperatures of each of the respective phases when they are first brought into contact during the manufacture of the bar be greater than 2. For example, if the discontinuous phase particles and noodles of the cintinuous phase soap mass are combined in the vacuum chamber of a two stage plodder prior to final extrusion, the hardness of the two phases should iffer by at least a factor of two.

It has been found that when this requirement is met, the discontinuous phase can be added as a sufficiently hard solid during high speed extrusion so that it does not undergo excessive deformation and homogenization. It has also been found that this requirement of λ>2.0, also helps the discontinuous phase to remain prominent at the surface of the bar after stamping without the need for wasteful trimming.

Water-soluble or Water-dispersible Matrix

A key component of the discontinuous phase is a surfactant that is solid at room temperature. The surfactant may be any of those described above in connection with the continuous phase. The surfactant is present in the discontinuous phase at a level between 1 and about 85 Wt %, preferably between 30 and 75 wt %, more preferably 50 and 75%.

A number of surfactants are suitable as a component of the dispersed phase matrix and, as noted above, most of the surfactants described above for the continuous phase can be employed here as well.

Particularly useful matrix surfactants are the sodium, potassium and triethanolamine soaps of long chain (C10–C18) fatty acids, acyl isethionate especially cocoyl isethionate, alkyl taurates, alkyl suflates and sulfonates, alkyl ethoxy sulfates, long chain alkyl ethoxylates, alkylglycosides, fatty acid esters of glycerol and sorbitol, and mixtures thereof.

Another useful matrix forming material is polyalkylene glycol having a melting point above 30° C. Preferably, the polyalkylene glycol should have a molecular weight greater than 4,000 to about 100,000, preferably 4000 to 20,000, most preferably 4000–10,000. Minimum MW of about 4000 is believed required so that carrier is solid at room temperature. An especially preferred carrier is polyethylene glycol, for example Carbowax PEG 8000, RTM® from Union Carbide.

Hydrophobically modified polyalkylene glycol (HMPAG) having broad molecular weight 4,000 to 25,000, preferably 4,000 to 15,000 can also be employed. Generally, the polymers will be selected from polyalkylene glycols chemically and terminally attached by hydrophobic moieties, wherein the hydrophobic moiety can be derivatives of linear or branched alkyl, aryl, alkylaryl, alkylene, acyl (e.g., preferably $C_8$ to $C_{40}$; fat and oil derivatives of alkylglyceryl, glyceryl, sorbitol, lanolin oil, coconut oil, jojoba oil, castor oil, almond oil, peanut oil, wheat germ oil, rice bran oil, linseed oil, apricot pits oil, walnuts, palm nuts, pistachio nuts, sesame seeds, rapeseed, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, etc. The total content of the hydrophobic moiety is preferably 3% wt. to 15% wt. per mole of the defined HMPAG.

Fatty acids, fatty acid esters, and fatty alcohols can be incorporated as part of the matrix forming the discontinuous phase as long as the matrix remains water soluble or water dispersible. Generally, the fatty group has a chainlength between 12 and 22 carbon atoms. Particularly suitable fatty acid esters is glycerol monolaurate.

Still other useful matrix materials in the invention are derived from polysaccharides especially starch. These include unmodified starch; starch modified to alter its water solubility, dispersability, and swelling, and hydrolyzed starch such as maltodextran.

Hardening Agents

As with the continuous phase It is may be possible to tailor the surfactant base of the discontinuous phase so that its hardness falls in the range required to mass-produce by high speed extrusion a multi-phase bar with an artisan crafted appearance. This can be done, for example, by adjusting the titre of the fat charge to achieve a harder mass, e.g., by hydrogenation or by manipulating the water content. However, this can compromise user properties and/or impact cost. Consequently, it is often beneficial to employ a hardening agent in the discontinuous phase.

Polyols and inorganic electrolytes are useful hardening agents when the discontinuous phase is comprised predominantly of fatty acid soaps. Polyols are defined here are molecules having multiple hydroxyl groups. Preferred polyols include glycerol, propylene glycol, sorbitol, and polyvinyl alcohol.

Preferred inorganic electrolytes include monovalent chloride salts, especially sodium chloride; monovalent and divalent sulfate salts like sodium sulfate; sodium carbonate; monovalent aluminate salts, monovalent phosphates, phosphonates, polyphosphate salts; and mixtures thereof. Further, the bar composition of the invention may include 0 to 25% by weight of crystalline or amorphous aluminium hydroxide. The said aluminium hydroxide can be generated in-situ by reacting fatty acids and/or non-fatty mono- or polycarboxylic acids with sodium aluminate, or can be prepared separately by reacting fatty acids and/or non-fatty mono- or polycarboxylic acids with sodium aluminate and adding the reaction product to the soap.

Another class of hardening agents are insoluble inorganic or mineral solids that can structure the discontinuous phase by network formation or space-filling. These include fumed, precipitated or modified silica, alumina, calcium carbonate, kaolin, and talc. Alumino-silicate clays especially synthetic or natural hectorites can also be used.

Optional Ingredients

In addition to the ingredients described above, the bar can also contain a variety of optional ingredients used to increase its shelf life, aesthetics or functionality. The ingredients can be found in continuous or discontinuous phase. These include chelating agents such as EDTA, preservatives like dimethyloldimethylhydantoin (Glydant XL 1000), parabens, sorbic acid antioxidants such as, for example, butylated hydroxytoluene (BHT) and a variety of natural and synthetic perfume components. Particularly useful optional ingredients are skin benefit agents used to deliver some useful end benefit to the skin and optical modifiers used to confer a unique appearance to the bar.

Skin Benefit Agents

The first class of ingredients and nutrients used to moisturize and strenghten the skin. These include:

a) vitamins such as vitamin A and E, and vitamin alkyl esters such as vitamin C alkyn esters;

b) lipids such as cholesterol, cholesterol esters, lanolin, cerimides, sucrose esters, and pseudo-ceramides;

c) liposome forming materials such as phospholipids, and suitable smphiphilic molecules having two long hydrocarbon chains;

d) esstetial fatty acids, poly unsaturated fatty acids, and sources of these materials;

e) triglycerides of unsaturated fatty acids such as sunflower oil, primrose oil, avocado oil, almond oil;

f) vegetable butters formed from mixtures of saturated and unsaturated fatty acids such as Shea butter;

g) mineral such as sources of zinc, magnesium, and iron;

A second type of skin benefit agent is a skin conditioner used to provide a moisturized feel to the skin. Suitable skin conditioners include:

a) silicone oils, gums and modifications thereof such as linear and cyclic polydimethylsiloxanes, amino, alkyl, and alkylaryl silicone oils;

b) hydrocarbons such as liquid paraffins, petrolatum, vasaline, microcrystalline wax, ceresin, squalene, pristan, paraffin wax and mineral oil;

c) conditioning proteins such as milk proteins, silk proteins and glutins;

d) cationic polymers as conditioners which may be used include Quatrisoft LM-200 Polyquaternium-24, Merquat Plus 3330-Polyquaternium 39; and Jaguar® type conditioners.

e) humectants such as glycerol, sorbitol, and urea f) emmolients such as esters of long chain fatty acids, such as isopropyl palmitate and cetyl lactate;

A third type of benefit agent is a deep cleansing agents. These are defined here as ingredients that can either increase the send of refreshment immediately after cleansing or can provide a sustained effect on skin problems that are associated with incompete cleansing. Deep cleansing agents include:

a) antimicrobials such as 2-hydroxy-4,2',4'-trichlorodiphenylether (DP300), 2,6-dimethyl-4-hydroxychlorobenzene (PCMX), 3,4,4'-trichlorocarbanilide (TCC), 3-trifluoromethyl-4,4'-dichlorocarbanilide (TFC), benzoyl peroxide, zinc salts, tea tree oil, b) anti-acne agents, such as salicylic acid, lactic acid, glycolic acid, and citric acid, and benzoyl peroxide (also an antimicrobial agent), c) oil control agents including sebum suppressants, mattifiers such as silica, titanium dioxide, oil absorbers, such as microsponges, d) astringents including tannins, zinc and aluminum sales, plant extracts such as from green tea and Witchhazel (Hammailes), e) scrub and exfolliating particles, such as polyethylene spheres, agglomerated silica, sugar, ground pits, seeds, and husks such as from walnuts, peach, avocado, and oats, salts, f) cooling agents such as menthol and its various derivatives and lower alcohols g) fruit and herbal extracts h) skin calming agents such as aloe vera i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geranoil, evening primrose, camphor, thymol, spirantol, penene, limonene and terpenoid oils;

Other benefit agents that can be employed include anti-ageing compounds, sunscreens, and skin lightening agents.

When the benefit agent is oil, especially low viscosity oil, it may be advantageous to pre-thicken it to enhance its delivery. In such cases, hydrophobic polymers of the type described in U.S. Pat. No. 5,817,609 to He et al may be employed, which is incorporated by reference into the subject application.

The benefit agent generally comprises about 0–25% by wt. of the composition, preferably 5–20%, and most preferably between 2 and 10%. Although the benefit agent can be added to either phase of the bar, in some cases it is especially desired to add the benefit agent to the discontinuous phase.

A final group of optional ingredients is optical modifiers which are defined as materials that modify the optical texture or transparency of the phases or introduce a pattern to increase the distinctiveness of one or both of the phases. Examples of suitable optical modifiers include:

a) transparency enhancing solvents such as glycerol, propylene glycol, sorbitol, or triethanolamine, b) speckles/bits such as ground fruit pits, seeds, polyethylene beads, mineral agglomerates, and loofha, c) reflective plate-like particles such as mica, d) pearlizing agents such as coated micas, and certain waxes e) wax/plastic slivers that resemble for example fruits slices, f) Vegetable or fruit slivers g) mattefiers such as $TiO_2$ h) mixtures of the above Further, either the continuous or phase can be made multicolored, e.g., striped, through the judicious use of dye as is well known in the art.

Bar Properties

In addition to the ratio of hardness of continuous phase to discontinuous phase, λ, described about, it is also critical to the invention that the bar have a descriptive visual scoring of at least 3.0 measured by a visual discrimination panel test as defined below:

The bars of the invention also preferably should have a certain plasticity. This is defined such that the continuous phase has a plastic radius measured in a three-point test for plasticity or brittleness also described below. The plastic radius of the continuous phase should be greater than 2 mm, preferably greater than 2.5 when measured at temperature of 40° C. in this test.

Test Methodology

Bar Hardness

A variety of methods are known in the art to measure the hardness of soft solids such as toilet soaps. Two techniques have been used here, the Cylinder Impaction test which measures the maximum force before yielding and the Penetration Test which measures the penetration of a needle under a constant load. Although the invention is described by parameters that measured by the Cylinder Impaction Test, this was done for convenience from a manufacturing perspective. The various hardness tests can obviously be inter-correlated.

Cylinder Inpaction Test for Hardness

The hardness of the continuous and dispersed phase was measured on extruded and compacted samples using the Cylinder Impaction Test employing a modified Crush-Test protocol that is used for measuring carton strength. A Regmed Crush Tester was employed.

Samples (typically 8×5×2 cm) at the desired temperature were placed on the lower plate of the tester fitted with a pressure gauge and a temperature probe inserted in the sample approximately 4 cm from the test area. An 89 gm inox metalic cylander (2.2 cm in.diameter (0.784 in) and 3 cm in length (1.18 in)) was placed at a central location on the top of the sample. The upper plate was then lowered to just touch cylinder.

The top plate was then lowered at a programmed rate of 0.635±0.13 mm/s (0.025±0.005 in/s ). At a certain strain, the sample will yield, bend or fracture and the maximum force expressed as PSI (lbs/inch$^2$) and average sample temperature are recorded. The water content of the sample was measured immediately after the test by microwave analysis. The hardness measurement was repeated a total of 3 times with fresh samples and an average taken. It is important to control the temperature and water content of the sample since hardness is sensitive to both these variables.

Penetration Test

A model PNR 10 penetrometer manufactured by FUR Berlin was employed Three standard cones (needles) are available; 2.5 g (18-0063), diameter: 0.9–3.05 mm, length: 79 mm. The measurement was carried out as follows. The cone is moved nearer to the surface of the test mass at the desired temperature with the coarse cone adjustment knob and then moved to just touch the surface of the test material with the fine cone adjustment knob. The start button is then pressed, releasing the cone—weighing 100 g for a time period of 60 sec at which time the penetration distance that the cone travels in the sample is measured and shown on a displacement gauge display. The reset button is pressed and the cone is lifted back to its zero position.

Three-Point Bend Test for Plasticity or Brittleness

The plastic zone radius or plasticity (brittleness) of the continuous and dispersed phase was measured using the standard Three-Point Bend Test. The Instron 5567 Material testing machine with the three-point bend rig attachment was used to obtain force and displacement data. The three-point bend test rig, mounted on the Instron 5567 machine, consisted of a hemispherical indenter and two static hemispherical supports. The span distance between the support was 6 inches.

Three types of three-point bend test measurements were needed for each sample in order to obtain the plasticity: un-notched bar, notched bar, and indentation tests.

Extruded soap samples were wrapped in plastic and equilibrated at 40° C. in an oven overnight. They were then placed one by one upon the static supports. For the un-notched test, the indenter was set in a position above the sample and then set automatically in motion at a 5 mm/min speed.

The notched test was carried out the same way, except that a notch was cut in the underside of the sample opposite to the indenter. For the indentation test, the soap sample was placed on a flat surface and the indentation bar was lowered at a 1 mm/min speed. The test was stopped when the force exceeded the peak force obtained from the un-notched test. Force and displacement data for the three tests were recorded in triplicates on a PC for further analysis and parameter computation. The plastic zone radius, r, provides the desired measure of plasticity and was calculated using Irwin's analysis. This may be found in T. L. Anderson's treatise "Fracture Mechanics Fundamentals and Application", pages 72–99, CRC Press (Boca Raton, Fla., 1995) and a copy of this is being incorporated by reference into the subject application.

It is desirable that the plastic radius of the continuous phase be greater than 2.0 cm, preferably greater than 2.5 cm, and most preferably greater that 3 cm.

Controlled Rubbing Test

The intrinsic wear rate of the discontinuous phase is measured by the following procedure.

a) Prepare a sample of discontinuous phase of the approximate dimensions: 7.5 cm long×5.5cm wide×2.3 cm thick
b) Measure and record the surface area of the face of each sample in square cm.
c) Record the weight of each bar prior to being washed.
d) Adjust the faucet water to 105° F. (40° C.) and keep it running into a vessle.
e) Immerse the bar and hands into the vessle.
f) Remove the bar from the water and rotate twenty (20) half turns.
g) Repeat steps d–f.
h) Immerse the bar for a third time and place into a soap dish.
i) Add 7.5 ml of water to the soap dish.
j) Repeat the wash procedure (steps c–g) three additional times during the first day. The washes should be spaced evenly throughout the work day.
k) After the last wash of the day, add 7.5 ml of water to the soap dish and let the bar sit overnight.
l) The following morning repeat the wash procedure (steps ii through vi) then place the bar sideways on a drying rack.
m) Allow the bar to sit for 24 hours then weigh the bar to the nearest 0.01 gm. The results are expressed as the accumulated weight loss divided by the surface area of the face.

Soap Transparency Test

The degree of transparency was measured using a light transmission tester model EVT 150 manufactured by DMS—Instrumentacao Cientifica Ltd. The instrument consists of a light source providing a 1.5 cm circular beam, a detector fitted to an analog meter, and a sample holder. The measurement procedure is as follows.

The instrument is first set to 100% transmission in air (i.e., without a test sample). The test sample of the bar material, approximately 90 g, having a thickness of 3 cm is placed in the sample chamber and the % transmission relative to air is measured. Normal opaque soap bars have 0% transmission, while translucent bars have a transmission ranging from about 5 to about 40%. Highly transparent bars such as those made by melt-cast processes have a transmission generally greater than 45%.

It has been found that discontinuous phase compositions having a % transmission difference relative to the continuous phase of greater than about 5% are perceived as visually distinctive. Preferably, the difference in light transmission between the phases should be greater than 10%.

Visual Discrimination Panel Test

Five bar samples taken at different times in a single test run are placed on a neutral gray background in a conventional viewing box. Above the test samples are placed high quality color photographs of "standard bars" that are agreed by a panel of five experts represent each "grade" in the following 5-point descriptive visual grading scale:

Descriptive Visual Grading Scale

1—poor: 2 phases not discernable

2—ordinary: smeared non-distinct boundary, some fine striations

3—above average: 2 phases evident but some smearing and loss of contrast

4—very good: 2 phases evident, sharp contrast but slight smearing at phase boundary 5—excellent: 2 phases evident, sharp contrast with little or no smearing 10 panelists (mix of expert and naive) evaluated the set of five samples and assigned a forced choice integer grade. They were instructed to mentally integrate overall surface appearance, quality and distinctiveness of the set in assigning a single grade. For each set of 5 bars, the average value across panelists is taken.

Bar Manufacture

The continuous soap phase is produced in standard toilet soaps finishing line using processing techniques and equipment well known in the art.

The first step of this process involves the mixing of dried soap noodles from the storage silos with the minor ingredients in a batch mixer. The objective of this operation is to generate a good distribution of the minor ingredients throughout the bulk of the soap batch until uniform coating of the noodles has occurred.

After mixing, the soap mass is generally passed through a refiner followed by a roll mill to achieve micro-mixing and improve composition uniformity.

Finally the soap will be further refined and plodded, usually under vacuum in a two-stage operation with a single or twin worm configuration with an intermediate vacuum chamber, and extruded as a bar for cutting and stamping. Both the final refiner and plodder stages play a part in completing the total mixing process by providing additional micro-mixing.

The discontinuous phase can also be produced as noodles in a conventional toilet bar making equipment but with a different composition than the continuous phase adequate to meet the hardness requirements.

The discontinuous phase is typically stored, for example, in a buffer hopper, generally at 25° C. After suitable tempering, it is combined with (e.g., added onto) the continuous soap phase which is at a temperature between 33° and 50° C., preferably 33° and 42° C. typically, in the vacuum chamber, between the refining and extrusion stages, by means of dosing equipment which controls its rate of delivery. For this purpose, the vacuum chamber is modified to receive the discontinuous soap phase stream.

The composite mass, (i.e., combining of continuous and discontinuous phase masses) is then compacted and extruded into billets which are then cut and stamped into the desired shape.

If done under vacuum, this vacuum is typically applied during mixing and refining, until the combined masses are extruded through, for example, a nosecone. Typically the vacuum is at 500 to 600 mm pressure (measured as mercury or Hg pressure).

Except in the operating and comparative examples, or where otherwise explicitly indicated, all numbers in this description indicating amounts or ratios of materials or conditions or reaction, physical properties of materials and or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

All percentage used, unless indicated otherwise, are intended to be percentages by weight.

EXAMPLES

EXAMPLE 1

This example illustrates the criticality of the hardness and plasticity of the continuous phase on bar appearance and manufacturability. The composition of the discontinuous phase used to prepare the bar examples 1A and 1B and comparative examples C1, C2 and C3 is shown in Table 1A. The hardness of this composition measured at 25° C. is 6.55 bars.

TABLE 1A

Composition of discontinuous phase

| Ingredient | Wt % |
|---|---|
| Sodium soap, Anhydrous (85/15 Talllow/Coco) | 70.45 |
| Ethane hydroxy diphosphoric acid (EHDP) | 0.02 |
| Ethylenediaminetetra acetic acid (EDTA) | 0.02 |
| Coconut Fatty Acids | 1.25 |
| Thriethanolamine | 1.5 |
| Propylene Glycol | 1.5 |
| Glycerol | 9.0 |
| Sodium Chloride | 1.26 |
| Perfume | 1.5 |
| Water | 13.5 |

The compositions of the continuous phases for Examples 1A and 1B and comparative examples C1, C2 and C3 are given in Table 1B. Bars were prepared from at a 5 kg scale using a 100 mm plodder by the process described in the Bar Manufacture Section.

The key physical properties of the continuous and dispersed phases (hardness, plastic radius, and hardness ratio) and the characteristics of the resulting bars (visual appearance and estimated line speed) are collected in Table 1C. Of the five samples only examples 1A and 1B have the three parameters of hardness and plastic ratio of the continuous phase and hardness ratio in the range of the invention. These samples indeed combine an artisan appearance (two distinctive domains—no cracks and fissures) with the potential for high speed manufacture (a line speed of at least 200, preferably at least 300 BPM).

TABLE 1B

Compositions and physical properties of continuous phases for Example 1

| Sample No. | C1 | C2 | C3 | Example 1A | Example 1B |
|---|---|---|---|---|---|
| INGREDIENTS | | | | | |
| Sodium soap, Anhydrous (85/15 Tallow/Coco) | 83.5 | 80.0 | 73.5 | 78.19 | 82.96 |
| EDTA | 0.02 | 0.02 | 0.02 | 0.02 | 0.02 |
| EHDP | 0.02 | 0.02 | 0.02 | 0.02 | 0.02 |
| Titanium Dioxide | 0.4 | — | — | — | — |
| Fluorescer | 0.024 | — | — | — | — |

TABLE 1B-continued

Compositions and physical properties of continuous phases for Example 1

| Sample No. | C1 | C2 | C3 | Example 1A | Example 1B |
|---|---|---|---|---|---|
| Coconut Fatty Acids | — | 4.0 | 0.5 | — | 1.0 |
| Glycerol | 0.2 | 0.2 | 0.2 | 2.0 | 0.2 |
| Sunflower seed oil | — | — | — | 2.0 | — |
| Silicone | — | — | — | 2.0 | — |
| Calcium Carbonate | — | — | 10.0 | — | — |
| Sodium Chloride | 0.8 | 0.78 | 0.76 | 0.77 | 0.8 |
| Perfume | 1.5 | 1.5 | 1.5 | 1.5 | 1.5 |
| Water | 13.5 | 13.5 | 13.5 | 13.5 | 13.5 |

TABLE 1C

Physical characteristics, surface appearance, line speeds

| Sample | C1 | C2 | C3 | Example 1A | Example 1B |
|---|---|---|---|---|---|
| Hardness (bar) continuous phase @ 37.5 C | 2.14 | 1.2 | 1.9 | 2.07 | 2.24 |
| Plastic radius, r | 1.9 | 3.8 | 1.1 | 2.6 | 2.8 |
| Hardness Ratio, λ (Cylinder Impaction Tests) | 3.1 | 5.4 | 3.4 | 3.2 | 2.9 |
| Penetration value of continuous phase @ 33 C | | | 17 mm | 14 mm | |
| Hardness ratio by Tenetration test | | | 4.4 | 2.6 | |
| Visual Grade[a] | 2.2 | 3.3 | 2.4 | 4.8 | 3.1 |
| Approximate line speed (bars per minute) | 390 | 100 | 300 | 425 | 350 |

[a]Descriptive Visual Grading Scale
1 - poor: 2 phases not discernable
2 - ordinary: smeared non-distinct boundry, some fine striations
3 - above average: 2 phases evident but some smearing and loss of contrast
4 - very good: 2 phases evident, sharp contrast but slight smearing at phase boundary
5 - excellent: 2 phases evident, sharp contrast with little or no smearing

EXAMPLE 2

This example illustrates the criticalities of the hardness ratio, λ as controlled by variations in the hardness of the discontinuous phase. Bar examples 2A–2C, and comparative examples C4 and C5 were prepared by the methods used in Example 1. The composition of the continuous phase used for all samples is shown in Table 2A.

TABLE 2A

Composition of the continuous phase for Bar Examples 2A–2C and comparative bar examples C4 and C5.

| INGREDIENT | Wt % |
|---|---|
| Sodium soap, Anhydrous | 77.77 |
| EDTA | 0.02 |
| EHDP | 0.02 |
| Titanium Dioxide | 0.4 |
| Fluorescer | 0.024 |
| Perfume | 1.5 |
| Silicone | 2 |
| Glycerine | 2 |
| Sunflower Oil | 2 |
| Sodium Chloride | 0.77 |
| Water | 13.5 |
| Hardness @ 37.5 C (bar) | 2.07 |

The compositions of the discontinuous phases used in this example, the relevent hardness ratios and the visual appearance of the bars formed from these phases is shown in Table 2B.

The multiphase bar examples 2A and 2B have hardness ratios, λ, greater than 2.5 and have a distinctive artisan crafted appearance and excellent quality in terms of surface appearance. In contrast comparative samples C4, C5, and C6 whose hardness ratios are less than 2.0 have poorer definition between the phases and have a more ordinary appearance.

TABLE 2B

Compositions and physical properties of discontinuous phases and visual appearance of bars made by combing these phases with the continuous phase of Table 2A.

| Sample No. INGREDIENTS | Example 2A | Example 2B | C4 Wt % | C5 | C6 |
|---|---|---|---|---|---|
| Sodium soap, Anhydrous (85/15 Tallow/Coco) | 70.38 | 74.46 | 75.7 | 77.96 | 80.0 |
| EDTA | 0.02 | 0.02 | 0.02 | 0.02 | 0.02 |
| EHDP | 0.02 | 0.02 | 0.02 | 0.02 | 0.02 |
| Titanium Dioxide | — | — | 0.4 | — | — |
| Fluorescer | — | — | 0.024 | — | — |
| Coconut Fatty Acids | 1.25 | 0.5 | — | 2.0 | 5.0 |
| Glycerol | 9.02 | 6.0 | 2.0 | — | — |
| Sunflower seed oil | — | — | 4.0 | — | — |
| Silicone | — | — | 2.0 | — | — |
| Thriethanolamine | 1.5 | — | — | — | — |
| Propilene Glycol | 1.5 | — | — | — | — |
| PEG | — | — | — | 5.0 | — |
| Sodium Chloride | 1.26 | | 0.77 | | — |
| Perfume | 1.55 | 1.50 | 1.50 | 1.50 | 1.50 |
| Water | 13.5 | 17.5 | 13.5 | 13.5 | 13.5 |
| Hardness at 25° C. | 6.55 | 5.86 | 4.13 | 3.44 | 3.44 |
| Hardness ratio (λ) | 3.1 | 2.8 | 1.9 | 1.7 | 1.7 |
| Visual Grade[a] | 4.8 | 3.1 | 2.4 | 2.0 | 1.6 |

a) Descriptive Visual Grading Scale

1—poor: 2 phases not discernable

2—ordinary: smeared non-distinct boundry, some fine striations

3—above average: 2 phases evident but some smearing and loss of contrast

4—very good: 2 phases evident, sharp contrast but slight smearing at phase boundary 5—excellent: 2 phases evident, sharp contrast with little or no smearing

EXAMPLE 3

This example illustrates several optical texture and pattern modifiers. The continuous phase is the same as used in Example 2. The discontinuous phases and appearance modifiers used in Samples 3A–3D are given in Table 3A. Bars were prepared by the methods set forth in Example 1.

TABLE 3A

Discontinuous phases for Example 3

| Discontinuous phases | Example 3A | Example 3B | Example 3C Wt % | Example 3D | Example 3E |
|---|---|---|---|---|---|
| INGREDIENTS | | | | | |
| Sodium soap, Anhydrous | Up to 100 | Up to 100 | Up to 100 | Up to 100 | Up to 100 |
| EDTA | 0.02 | 0.02 | 0.02 | 0.02 | 0.02 |
| EHDP | 0.02 | 0.02 | 0.02 | 0.02 | 0.02 |
| Coconut Fatty Acids | 0.5 | 1.25 | 1.25 | 0.5 | 0.5 |
| Glycerol | 6.0 | | 9,01879 | 8.0 | 8.0 |
| Sunflower seed oil | — | — | — | — | — |
| Silicone | — | — | — | — | — |
| Sodium Chloride | | 1.26 | 1.26 | | |
| Perfume | 1.50 | 1.55 | 1.55 | 1.50 | 1.50 |
| Water | 17.5 | 13.5 | 13.5 | 17.5 | 17.5 |
| APPEARANCE MODIFIERS | | | | | |
| $TiO_2$ | 0.2 | | | | |
| Speakles[a] | — | — | 1.0 | 1.0 | — |
| Mica[b] | | — | — | 0.3 | 0.3 |
| Glycerol | | 9.02 | 9.02 | | |
| Propylene glycol | | 1.5 | 1.5 | | |
| Triethanolamine | | 1.5 | 1.5 | | |
| Hardness at 25° C. | 85 | 95 | 99 | 89 | 85 |
| Hardness Ratio, λ | 2.6 | 3.0 | 3.1 | 2.8 | 2.6 |

[a]Speckles - agglomerated bentonite granules
[b]Mica - Timiron and/or Mercare Interference Pigment The appearance of bars made with the discontinuous phases are described in Table 3B. All have an artisan-crafted appearance but provide different textures and impressions

TABLE 3B

Appearance of bar Examples 3A–3E.

| | Example 3A | Examples 3B | Examples 3C | Examples 3D | Examples 3E |
|---|---|---|---|---|---|
| Appearance of dis-continuous phase | Opaque white streaks | Trans-lucent chunks | Speckled translucent chunks | Speckled opaque pearlized pools | Opaque pearlized pools |
| Hardness Ratio, λ | 2.5 | 3.0 | 3.1 | 2.8 | 2.8 |

EXAMPLE 4

Table 4 illustrates other discontinuous phase compositions having the physical properties described herein.

TABLE 4

Discontinuous phase compositions

| Sample No. Ingredients | 4A | 4B | 4C Wt % | 4D |
|---|---|---|---|---|
| Matrix | | | | |
| PEG (MW8000) | 74 | 35 | 35 | |
| Cocoyl isethionate | 1.5 | 30 | 30 | 50 |
| C16/C18 fatty acid | 14.5 | 18 | | 15 |
| Maltodextran | | 10 | 10 | |
| Na tallowate | | | | 5 |
| glycerol monolaurate | | | 18 | |
| Paraffin wax | | | | 20 |

TABLE 4-continued

Discontinuous phase compositions

| Sample No. Ingredients | 4A | 4B Wt % | 4C | 4D |
|---|---|---|---|---|
| silica | 1.5 | | | |
| Water and minors | to 100% | to 100% | to 100% | to 100% |

wherein the bar has a descriptive visual grading score of at least 2.6 when measured by Visual Discrimination Panel Test; wherein the temperatures noted approximately reflect the thermal condition of each phase during the time of extrusion.

What is claimed is:

1. A process for making a multiphase soap bar having an artisan appearance comprising the steps of:

a) adding to noodles comprising the continuous phase of a toilet bar mass that has a penetrometer hardness value of 1.9 to 2.5 bar measured at a temperature about 33 to 50° C., a second solid mass that is in the form of descrete particles having at lease one dimension greater than 3 mm to form a mixture, wherein at the time of addition, the hardness of the said second solid mass is at least twice the hardness of the noodles forming the continuous phase toilet bar mass, said hardness values measured by the Cylinder Impaction Test;

b) extruding the mixture so formed in step 1) to form an extruded composite mass comprising a continuous toilet bar mass and a discontinuous phase of the second solid mass;

c) cutting and forming the extruded mass into a bar wherein the discontinuous phase comprises 1 to about 25 wt % of the bar, and wherein the bar has a descriptive visual grading score of at least 3.0 when measured by Visual Discrimination Panel Test and altered rheological phases.

2. A process according to claim 1 wherein steps a) and b) are done under a vacuum of 500–600 mm Hg.

3. A process according to claim 1 wherein the toilet bar mass has a plastic radius greater than 2 mm measured at a temperature of 40° C. in a three point bend test.

4. A process according to claim 1 wherein the continuous phase and disperse phase of said bar have a difference in transparency of at least 5%.

5. A process according to claim 1 wherein the toilet bar mass comprises a) 25 to 85 wt % of a surfactant base selected from the group consisting of fatty acid soaps, syndets and their mixture, and b) to 15 wt % of a plasticizing agent selected from the group consisting of fatty acids, glycerol, propylene glycol, thriethanolamine, hydrocarbon oils, vegetable oils, silicone oils, waxes, fatty alcohols, glycerol derivatives, sorbitol derivatives, nonionic surfactants, and mixtures thereof.

6. A process according to claim 1 wherein the solid mass comprises a) 1–70 wt % surfactant selected from the group consisting of fatty acid soap, acyl isethionate, alkyl suflates, alkyl ethoxy sulfates, alkyl ethoxylates, alkylglycosides, and mixtures thereof b) 0–15% of a hardening agent selected from the group consisting of polyols, inorganic electrolytes, silica, alumina, talc, and mixture thereof c) 0 to 90 wt % of a matrix forming material selected from the group consisting of polyethers having a melting point above 30° C., fatty acids, fatty alcohols, fatty acid polyol esters, starch, hydrolyzed starch, maltodextran and mixtures thereof.

* * * * *